United States Patent [19]

Pinkos et al.

[11] Patent Number: 5,436,335
[45] Date of Patent: Jul. 25, 1995

[54] PREPARATION OF 2,6-DIMETHYLMORPHOLINE FROM N-(2-HYDROXYPROPYL)-2,6-DIMETHYL-MORPHOLINE

[75] Inventors: Rolf Pinkos, Bad Duerkheim; Hans R. Merkle, Ludwigshafen; Rolf Fischer, Heidelberg, all of Germany

[73] Assignee: BASF Aktiengesellschaft, Ludwigshafen, Germany

[21] Appl. No.: 307,245

[22] Filed: Sep. 16, 1994

Related U.S. Application Data

[62] Division of Ser. No. 110,222, Aug. 23, 1993, abandoned.

[30] Foreign Application Priority Data

Aug. 29, 1992 [DE] Germany .......... 42 28 885.1

[51] Int. Cl.⁶ .......................................... C07D 265/30
[52] U.S. Cl. .......................................... 544/106; 544/175
[58] Field of Search .......................................... 544/106

[56] References Cited

U.S. PATENT DOCUMENTS

| | | |
|---|---|---|
| 3,083,202 | 3/1963 | Summers . |
| 3,151,112 | 9/1964 | Moss . |
| 3,413,292 | 11/1968 | Johnson . |
| 4,212,972 | 7/1980 | Goetz . |
| 4,298,733 | 11/1981 | Goetz . |
| 4,504,363 | 3/1985 | Goetz et al. . |
| 4,571,284 | 2/1986 | Mueller . |
| 4,739,051 | 4/1988 | Schroeder . |
| 4,778,886 | 10/1988 | Borsdorff . |

FOREIGN PATENT DOCUMENTS

| | | |
|---|---|---|
| 129904 | 1/1985 | European Pat. Off. . |
| 650380 | 9/1937 | Germany . |

*Primary Examiner*—Robert W. Ramsuer
*Attorney, Agent, or Firm*—Keil & Weinkauf

[57] ABSTRACT

A process for the preparation of 2,6-dimethylmorpholine from N-(2-hydroxypropyl)-2,6-dimethylmorpholine, in which N-(2-hydroxypropyl)-2,6-dimethylmorpholine, in which a) N-(2-hydroxypropyl)-2,6-dimethylmorpholine is caused to react in the presence of a catalyst containing an element listed in Groups Ib, IIb, and/or VIIIb of the Periodic Table at temperatures ranging from 150° to 600° C. and is then caused to react with water at temperatures ranging from 30° to 300° C. or b) N-(2-hydroxypropyl)-2,6-dimethylmorpholine is caused to react in the presence of an acid catalyst at temperatures ranging from 100° to 400° C. followed by acid hydrolysis with water at temperatures ranging from 30° to 300° C.

3 Claims, No Drawings

PREPARATION OF 2,6-DIMETHYLMORPHOLINE FROM N-(2-HYDROXYPROPYL)-2,6-DIMETHYLMORPHOLINE

This is a Division of application Ser. No. 08/110,222, filed Aug. 23, 1993, now abandoned.

The present invention relates to processes for the preparation of 2,6-dimethylmorpholine from N-(2-hydroxypropyl)-2,6-dimethylmorpholine by dehydrogenation or by the elimination of water followed by hydrolysis.

2,6-Dimethylmorpholine and N-(2-oxypropyl)-2,6-dimethylmorpholine, which has not been previously described, are desirable starting points for synthesis processes, e.g., for plant protectants and pharmaceuticals.

EP-A 94,565 describes a process for the preparation of 2,6-dimethylmorpholine, in which bis(2-hydroxypropyl)amine is obtained using stoichiometrically excessive amounts of sulfuric acid. In order to effect liberation of the 2,6-dimethylmorpholine, the sulfuric acid must be neutralized, thus enforcing the formation of sulfates.

It is thus an object of the present invention to overcome the aforementioned drawback.

Accordingly, we have found a novel and improved process for the preparation of 2,6-dimethylmorpholine from N-(2-hydroxypropyl )-2,6-dimethylmorpholine, wherein a) N-(2-hydroxypropyl)-2,6-dimethylmorpholine is caused to react in the presence of a catalyst containing an element listed in Groups Ib, IIb, and/or VIIIb of the Periodic Table at temperatures ranging from 150° to 600° C. and is then caused to react with water at temperatures ranging from 30° to 300° C.

b) N-(2-hydroxypropyl)-2,6-dimethylmorpholine is caused to react in the presence of an acid catalyst at temperatures ranging from 100° to 400° C. followed by acid hydrolysis with water at temperatures ranging from 30° to 300° C.

We have also found a novel compound, ie the compound N-(2-oxopropyl)-2,6-dimethylmorpholine.

The processes proposed herein may be carried out as follows:

In each case it is possible to use the cis- or trans-n-(2-hydroxypropyl)-2,6-dimethylmorpholine or, preferably, an isomer mixture thereof, as obtained in the cyclization of triisopropanolamine, a by-product (waste product) of the synthesis of diisopropylamine.

a) N-(2-hydroxypropyl)-2,6-dimethylmorpholine can be oxidized to form the N-(2-oxopropyl)-2,6-dimethylmorpholine at temperatures ranging from 150° to 600° C. in the liquid or gas phase and preferably at temperatures ranging from 280° to 400° C. in the gas phase and pressures of from 0.001 to 5 bar and preferably from 0.02 to 2 bar and more preferably under standard pressure conditions (atmospheric pressure).

Oxidation of N-(2-hydroxypropyl)-2,6-dimethylmorpholine to produce N-(2-oxopropyl)-2,6-dimethylmorpholine can be carried out using the usual oxidizing agents, as described or cited in Houben Weyl, Vol VII/2a (1973), e.g., manganese dioxide or chromium-(IV) compounds. Catalysts for catalytic dehydrogenations are preferred, such as Group Ib, Group IIb, and/or Group VIIIb elements as listed in the Periodic Table, in metallic form and more preferably in the form of oxides, or as combinations of metals and metal oxides.

Suitable catalysts containing elements listed in Groups Ib IIb, and/or VIIIb of the Periodic Table in the metallic form are copper, silver, gold, zinc, cadmium, iron; cobalt, nickel, ruthenium, rhodium, palladium, osmium, iridium, and platinum and preferably copper, silver, gold, ruthenium, rhodium, palladium, osmium, iridium, and platinum and more preferably copper, silver, and zinc.

Suitable catalysts containing elements listed in Groups Ib, IIb, and/or vIIIb of the Periodic Table in the form of the oxides are copper, silver, gold, zinc, cadmium, iron, cobalt, nickel, ruthenium, rhodium, palladium, osmium, iridium, and platinum and preferably copper, silver, gold, zinc, ruthenium, rhodium, palladium, osmium, iridium, and platinum and more preferably copper, silver, and zinc.

The reaction can be carried out with or without a carrier gas. Inert carrier gases are preferred such as hydrogen, nitrogen, or argon. If desired, oxygen or air can be added to the carrier gas up to a concentration of, say, 5%.

N-(2-oxopropyl)-2,6-dimethylmorpholine can be separated, by distillation, from unconverted 2N-(2-hydroxypropyl)-2,6-dimethylmorpholine and by-products The N-(2-oxopropyl)-2,6-dimethylmorpholine can be hydolyzed to form 2,6-dimethylmorpholine either in a purified form or directly from the dehydrogenation with water at temperatures ranging from 30° to 300° C. and preferably from 100° to 250° C. and pressures of from 0.01 to 50 bar and preferably from 0.5 to 20 bar and more preferably from 1 to 10 bar.

This may be carried out in the presence of conventional acid or basic catalysts such as dilute phosphoric or sulfuric acid or dilute caustic soda solution or dilute caustic potash solution. However, it is particularly preferred for the reaction to be carried out autocatalytically, ie, without the addition of catalysts,.

The molar ratio of water to the N-(2-oxopropyl)-2,6-dimethylmorpholine can be varied within wide limits such as from 500:1 to 0.5:1 and preferably from 50:1 to 1:1 and more preferably from 10:1 to 2:1.

When the process is carried out continuously, water can be removed by distillation together with 2,6-dimethylmorpholine, if necessary under pressure.

If conversion is not quantitative, the N-(2-oxopropyl)-2,6-dimethylmorpholine can be separated from 2,6-dimethylmofpholine by distillation and reused.

b) N-(2-hydroxypropyl)-2,6-dimethylmorpholine can be dehydrated to form N-(2-propenyl)-2,6-dimethylmorpholine and N-(1 -propenyl)-2,6-dimethylmorpholine by acid-catalyzed elimination of water in the liquid phase and preferably in the gas phase, over acid catalysts at temperatures ranging from 100° to 400° C. and preferably from 150° to 350° C. and more preferably at from 180° to 290° C. and pressures of from 0.01 to 2 bar and preferably from 0.05 to 1 bar. When the reaction is carried out in the gas phase, the residence time can be from, say, 1 to 5 s.

Water can be added to the feed in a concentration of from 0 to 10 mol and preferably from 0.01 to 1 mol, for each mole of N-(2-hydroxypropyl)-2,6-dimethylmorpholine.

Suitable acid catalysts are acid or superacid metal oxides of elements listed in Groups Ib, IIb, IVb, and VIIIb of the Periodic Table, preferably $TiO_2$)$ZrO_2$, $Fe_2O_3$, and ZnO or of elements listed in Groups IIa, IIIa, and IVa of the Periodic Table, preferably MgO, $B_2O_3$, $Al_2O_3$, $SiO_2$, and $SnO_2$ or combinations thereof, such as $TiO_2$/ZnO or $Al_2O_3$/MgO. In order to increase their acid strength, the oxides can be treated with acids such as sulfuric acid or phosphoric acid.

Other suitable acid catalysts are acid zeolites, for example representatives of the mordenite species or fine-pored zeolites of the erionite or chabazite species or zeolites of the faujasite species, e.g., type Y, type X or type L zeolites. This group also includes the so-called "ultrastable" zeolites of the faujasite species, ie, dealuminated zeolites.

Also suitable are zeolites having a pentasile structure such as ZSM-5, ZSM-11 and ZBM-10. These are all based on a five-membered ring composed of $SiO_2$ tetrahedra. They are characterized by a high $SiO_2$/$Al_2O_3$ ratio and by pore sizes which are between those of the A-type zeolites and those of the X or Y species.

Equally suitable are stratified silicates such as Tonsil, which can be doped with aluminum oxide, or alumosilicates.

Other suitable acid catalysts are heteropoly acids. These are inorganic poly acids, which, unlike isopoly acids, possess at least two different center atoms. There may be mentioned, as examples thereof, dodecatungstophosphoric acid $H_3PW_{12}O_{40}.H_2O$ and dodecamolybdophosphoric acid $H_3PMo_{12}O_{40}.H_2O$. In principle, catalysts and combinations of catalysts as cited in 158,229 can be used.

Preferred heteropoly acids are heteropoly acids of molybdenum or tungsten with phosphoric acid, telluric acid, selenic acid, arsenic acid, or silicic acid and especially with phosphoric acid.

The protons of the heteropoly acids can be partially replaced by metal ions, the alkali metal and alkaline earth metal ions being preferred.

In principle, combinations of said catalysts are suitable, e.g., combinations of aluminum oxides, which have been modified by acids such as sulfuric or phosphoric acid, and heteropoly acids.

The acid catalysts can, if desired, be doped with Group VIIb metals such as Pd.

The reaction products can be separated, by distillation, into water, N-(2-propenyl)-2,6-dimethylmorpholine, 2,6-dimethylmorpholine and any unconverted N-(2-hydroxypropyl)-2,6-dimethylmorpholine and propionaldehyde or derivatives thereof.

It is particularly preferred to admix the reaction products with an isomerisation catalyst for the isomerization of N-(2-propenyl)-2,6-dimethylmorpholine to produce N-(1-propenyl)-2,6-dimethylmorpholine and, optionally continuously, with water and to heat the mixture to from 25° to 250° C. and preferably to from 100° to 200° C.

Batchwise operations can be carried out in a pressure vessel, with establishment of autogenous pressure, or under distillation conditions, optionally under a pressure of up to 20 bar, the 2,6-dimethylmorpholine formed being removed by distillation.

The added amount of water can be from 0.5 to 10 mole-equivalents based on N-(2-hydroxypropyl)-2,6-dimethylmorpholine used. A suitable isomerisation catalyst can be, for example, Pd on activated charcoal, which can be added in a ratio, by weight, of from 0.001:1 to 0.3:1 with respect to the N-(2-hydroxypropyl)-2,6dimethylmorpholine used.

The elimination of water can be carried out in, say, fluid-bed reactors or, preferably, fixed-bed reactors.

The process is illustrated below with reference to the following examples, in which the percentages are by weight unless otherwise stated, as determined by gas chromatography using an internal standard. The N-(2-oxopropyl)-2,6-dimethylmorpholine or N-(2-hydroxypropyl)-2,6-dimethylmorpholine used were each in the form of a cis/trans-isomer mixture (cis:trans=60-80:40-20).

EXAMPLES

Examples of Method a)

Example 1

7 g of N-(2-hydroxypropyl)-2,6-dimethylmorpholine/h were caused to react over 10 g of extruded catalyst (ca 94% of ZnO, 4% of MgO, remainder CaO and NaO) in an N2-stream (4 L/h). At a temperature of 300° C., the effluent contained 7% of N-(2-oxopropyl)-2,6-dimethylmorpholine, 86.4% of N-( 2-hydroxypropyl)-2,6-dimethylmorpholine, 1.4% of N-(2-propenyl)-2,6-dimethylmorpholine, and 2.1% of 2,6-dimethylmorpholine. At a temperature of 350° C., the effluent contained 15.3% of N-( 2-oxopropyl)-2,6-dimethylmorpholine, 75.3% of N-( 2-hydroxypropyl)-2,6-dimethylmorpholine, 3.4% of N-(2-propenyl)-2,6-dimethylmorpholine, and 2.8% of 2,6-dimethylmorpholine. At a temperature of 380° C., 23.8% of N-(2-oxopropyl)-2,6-dimethylmorpholine, 61.1% of N-(2-hydroxypropyl)-2,6-dimethylmorpholine, 4.8% of N-(2-propenyl)-2,6-dimethylmorpholine, and 4.9% of 2,6-dimethylmorpholine were present in the effluent.

The ratio of the cis and trans isomers of the morpholine derivatives was about 7:3 in each case.

Example 2

1.5 g of N-(2-hydroxypropyl)-2,6-dimethylmorpholine/h were caused to react over 180 g of extruded ZnO catalyst at from 250° to 400° C. and under an N2-stream flowing at a rate of 18L/h. Following a period of 1–2 h, the effluents were produced at a rate of ca 15 g/h. The results are listed in the following table:

| Temp. [°C.] | NODM [%] | NHDM [%] | N-2-PM [%] | 2,6-DMM [%] |
|---|---|---|---|---|
| 250 | 33.9 | 41.9 | 4.5 | 3.3 |
| 290 | 33.9 | 54.4 | 2.8 | 0.7 |
| 320 | 53.6 | 26.3 | 5.9 | 2.2 |
| 350 | 70.2 | 15.4 | 4.1 | 1.2 |
| 370 | 72.4 | 5.2 | 3.8 | 2.5 |
| 400 | 73.0 | 1.6 | 3.7 | 2.8 |

NODM = N-(2-oxopropyl)-2,6-dimethylmorpholine;
NHDM = N-(2-hydroxypropyl)-2,6-dimethylmorpholine;
N-2-PM = N-(2-propenyl)-2,6-dimethylmorpholine;
2,6-DMM = 2,6-dimethylmorpholine.

Example 3

In a manner similar to that described in Example 2, 15 g/h of N-(2-hydroxypropyl)-2,6-dimethylmorpholine were caused to react over 142 g of znO at 350° C. over a period of 23 h. Some results are listed in the table below:

| Time [h] | NODM [%] | NHDM [%] | N-2-PM [%] | 2,6-DMM [%] | NODM [%] |
|---|---|---|---|---|---|
| 3 | 65.7 | 2.4 | 5.6 | 8.3 | 67 |
| 14 | 76.5 | 9.9 | 3.1 | 1.8 | 85 |
| 23 | 74.0 | 13.2 | 2.7 | 1.4 | 85 |

The collected effluents (340 g) were fractionally distilled in a packed column (10 theoretical trays). The isomeric N-(2-oxopropyl)-2,6-dimethylmorpholines boil, under a pressure of 1 mbar, at from 86° to 90° C.

N(2-oxopropyl)-2,6-dimethylmorpholine is clearly characterized by the mass spectrum, the $^1$H- and $^{13}$C-NMR spectra, and the infrared spectrum.

The IR data for the oxopropyls are given by way of example:

cis-N-(2-oxopropyl)-2,6-dimethylmorpholine: 2981, 2942, 2871, 2816, 1729, 1452, 1359, 1323, 1219, 1151,1082, 970, 879, 847, 775 cm$^{-1}$;

trans-N-(2-oxopropyl)-2,6-dimethylmorpholine: 2981, 2942, 2896, 2816, 1730, 1461, 1382, 1227, 1153, 1131, 1076, 1036, 973, 878, 850, 800 cm$^{-1}$.

Example 4

0.5 g of N-(2-oxopropyl)-2,6-dimethylmorpholine and 3 g of water were heated to 150° C. for 75 min in an autoclave. On cooling, 17.5mol % of 2,6-dimethylmorpholine and ca 81 mol% of educt were found.

Examples of Method b)

Example 5

28 mL of N-(-2-hydroxypropyl)-2,6-dimethylmorpholine were evaporated for 3 h under a blanket of nitrogen (14 mL/h, 250° C.) in a pre-evaporator and passed over SiO$_2$ extrudates (3 mm). At a reaction temperature of 250° C., there were present in the two-phase effluent (21) 56% of N-(2-propenyl)-2,6-dimethylmorpholine, 3% of 2,6-dimethylmorpholine, 15% of N-(1-propenyl)-2,6-dimethylmorpholine and 0.8% of educt. The remainder was essentially water.

5 g of this effluent were admixed with 1.5 g of water and 0.3 g of Pd(10%) on activated charcoal and heated to 150° C. for 1 h in an autoclave (5 bar autogenous pressure). There were obtained 20% of 2,6-dimethylmorpholine and 1.8% of N-(2-propenyl-2,6-dimethylmorpholine.

Example 6

34.2 g of N-(2-hydroxypropyl)-2,6-dimethylmorpholine were caused to react over 200 g of Al$_2$O$_3$ over a period of 5 h at 50 mbar and at a reaction temperature of 200° C. The effluent (33.3 g) was admixed with 2 g of Pd (10% ) on carbon and 10 g of water and heated at 150° C. for 2 h. There was obtained 27% of 2,6-dimethylmorpholine in addition to small amounts of N-(2-propenyl)-2,6-dimethylmorpholine.

We claim:

1. A process for the preparation of 2,6-dimethylmorpholine from N-(2-hydroxypropyl)-2,6-dimethylmorpholine, wherein N-(2-hydroxypropyl)-2,6-dimethylmorpholine is caused to react in the presence of an acid catalyst at temperatures ranging from 100° to 400° C. followed by acid hydrolysis with water at temperatures ranging from 30° to 300° C.

2. A process for the preparation of 2,6-dimethylmorpholine from N-(2-hydroxypropyl)-2,6-dimethylmorpholine as defined in claim 1, wherein the acid catalysts used are metal oxides, zeolites, stratified silicates, or heteropoly acids.

3. A process as defined in claim 2, wherein the acid catalysts include metals of Group VIIIb of the Periodic Table.

* * * * *